US012806051B2

(12) United States Patent
Hildebrand et al.

(10) Patent No.: US 12,806,051 B2
(45) Date of Patent: Nov. 24, 2026

(54) METHOD FOR EMBEDDING A BALLOON, ARRANGED ON A CATHETER, IN AN IMPLANT

(71) Applicant: BIOTRONIK AG, Buelach (CH)

(72) Inventors: Simon Hildebrand, Kreuzlingen (CH); Alexandros Haemmerli, Rüschlikon (CH)

(73) Assignee: BIOTRONIK AG, Buelach (CH)

( * ) Notice: Subject to any disclaimer, the term of this patent is extended or adjusted under 35 U.S.C. 154(b) by 113 days.

(21) Appl. No.: 18/915,746

(22) Filed: Oct. 15, 2024

(65) Prior Publication Data

US 2025/0032288 A1 Jan. 30, 2025

Related U.S. Application Data

(63) Continuation of application No. 16/339,266, filed as application No. PCT/EP2017/076962 on Oct. 23, 2017, now abandoned.

(30) Foreign Application Priority Data

Nov. 2, 2016 (EP) .................................... 16196869

(51) Int. Cl.
*A61F 2/958* (2013.01)
*B29C 65/02* (2006.01)
(Continued)

(52) U.S. Cl.
CPC .............. *A61F 2/958* (2013.01); *B29C 65/02* (2013.01); *A61F 2/9522* (2020.05);
(Continued)

(58) Field of Classification Search
CPC ............ A61F 2/9582; A61F 2002/9583; A61F 2240/001; A61F 2/9522–9526;
(Continued)

(56) References Cited

U.S. PATENT DOCUMENTS 5,718,973 A * 2/1998 Lewis ........................ A61F 2/82 623/1.1
6,063,092 A * 5/2000 Shin ........................ A61F 2/958 606/108
(Continued)

FOREIGN PATENT DOCUMENTS

DE 3324413 A1 * 1/1985
WO 2009009636 A1 1/2009

OTHER PUBLICATIONS

Machine Translation of Bartel (DE3324413A1), Espacenet, Jan. 24, 1985 (generated Feb. 3, 2022) (Year: 1985).*
(Continued)

*Primary Examiner* — Andrew L Swanson
(74) *Attorney, Agent, or Firm* — Greer, Burns & Crain, Ltd.; Steven P. Fallon

(57) ABSTRACT

A method for embedding a balloon, arranged on a catheter, in an implant having an open-work structure consists of: producing an assembly consisting of the catheter with the balloon and the implant mounted on the outer side of the balloon, inserting the assembly into a cavity of an embedding mold, which is lined on its inner wall with a protective film, wherein the protective film is strip-like, and a width of the protective film is greater than the circumference of the cavity, connecting the catheter to a fluid source, heating the embedding mold with the assembly in a heating element for a predefined time, applying internal pressure to the balloon by the fluid source, cooling the embedding mold with the assembly with a predefined second internal pressure in the balloon, deflating the balloon after cooling the embedding mold with the assembly, and removing the from the mold.

14 Claims, 2 Drawing Sheets

(51) Int. Cl.
*A61F 2/95* (2013.01)
*B29L 31/00* (2006.01)

(52) U.S. Cl.
CPC . *A61F 2002/9583* (2013.01); *A61F 2240/001* (2013.01); *B29L 2031/7543* (2013.01)

(58) Field of Classification Search
CPC .. B61F 2/952; B29C 65/02; B29L 2031/7543; A61M 25/1027
See application file for complete search history.

(56) References Cited

U.S. PATENT DOCUMENTS

| | | | | |
|---|---|---|---|---|
| 6,352,547 | B1 * | 3/2002 | Brown | B25B 27/146 606/1 |
| 6,981,982 | B2 * | 1/2006 | Armstrong | A61F 2/86 606/198 |
| 2006/0216404 | A1 * | 9/2006 | Seyler | A61F 2/95 427/2.1 |
| 2007/0006441 | A1 * | 1/2007 | McNiven | A61F 2/958 29/508 |
| 2011/0213451 | A1 | 9/2011 | Oepen et al. | |
| 2015/0040949 | A1 | 2/2015 | Zucker et al. | |
| 2021/0186555 | A1 * | 6/2021 | Bacino | A61M 25/1002 |

OTHER PUBLICATIONS

European Search Report for the corresponding European Patent Application No. 16196869.8, dated Apr. 7, 2017.

* cited by examiner

METHOD FOR EMBEDDING A BALLOON, ARRANGED ON A CATHETER, IN AN IMPLANT

PRIORITY CLAIM

This application is continuation of and claims priority under 35 U.S.C. 120 from U.S. application Ser. No. 16/339,266, filed Apr. 3, 2019, which application is incorporated by reference herein and was a 35 U.S.C. 371 US National Phase and claims priority under 35 U.S.C. § 119, 35 U.S.C. 365(b) and all applicable statutes and treaties from prior PCT Application PCT/EP2017/076962, which was filed Oct. 23, 2017, which application claimed priority from European Application EP 16196869.8, which was filed Nov. 2, 2016.

FIELD OF THE INVENTION

The invention relates to a method for embedding a balloon, arranged on a catheter, in an implant having a heating element, and to an associated device.

BACKGROUND

Within the context of the present invention, implants are to be understood to be endovascular prostheses or other endoprostheses, for example stents (vessel stents (vascular stents, including stents for use in the region of the heart and heart valve stents, for example mitral valve stents, pulmonary valve stents) and biliary duct stents), endoprostheses for closing persistent foramen ovale (PFO), stent grafts for the treatment of aneurysms, endoprostheses for closing an ASG (interatrial septum defect, atrial septal defect), and prostheses in the area of the hard and soft tissue. An implant of this type is often inserted via catheter into the organ or vessel to be treated.

Implants of this type in many cases have, at least in a portion, an open-work hollow-cylindrical (tubular) and/or hollow-conical structure, which is open at both longitudinal ends. The open-work structure is often composed of a plurality of struts, which are connected to one another and between which there are arranged continuous cutouts (gaps).

Such implants usually assume two states, specifically a compressed state with a small diameter and an expanded state with a larger diameter. In the compressed state, the implant can be introduced by the catheter into the vessel or organ to be treated, through narrow vessels, and can be positioned at the point to be treated. The implant is often mounted on a balloon of the catheter, i.e. on the outer side of the balloon, which balloon is also compressed. At the treatment site, the implant is then expanded by the balloon of the catheter so as to be transferred into the expanded state. The implant remains in the vessel or organ in the expanded state and is fixed there once the catheter has been removed from the body of the treated patient. As the implant is being transported through organs and vessels of the body to the treatment site in the compressed state, it is necessary that the implant sits firmly on the balloon and securely assumes the compressed state, so that the implant can be reliably guided to the treatment site, without damaging the vessels and organs through which it is passed. Furthermore, any damage to the filigree structure of the implant or the balloon or contamination of the implant or the balloon should be avoided. Contamination can occur in particular because many implants and/or balloons nowadays carry coatings which contain a therapeutically active material (medicament).

In order to arrange the implant on the balloon, the implant is fixed or mounted on the balloon, for example by crimping. However, the implant is only reliably held on the balloon by a process step referred to as embedding. In the case of embedding the balloon material is pressed or sunk into the gaps of the already-mounted implant. However, during this conventional embedding process, a strong inflation of the balloon or an expansion of the implant should be avoided.

Document US 2016/0096308 A1 discloses a heat exchanger, in which a pipe is arranged, for an embedding of this type of a stent in a balloon. The pipe serves to receive an assembly consisting of catheter with balloon and stent. This assembly is heated after arrangement thereof in the pipe in the heat exchanger, and the balloon is then pumped up via the catheter. The balloon is then held at a second temperature for a predefined period and is then cooled again In a similar method known from document U.S. Pat. No. 6,063,092, an assembly consisting of a stent and a catheter arranged therein with balloon is arranged in a Teflon sleeve provided with a longitudinal slit. This sleeve is additionally placed in a casing of reducible diameter, which can be heated. Together with this casing, the sleeve and the assembly are arranged and heated in a heating block. An internal pressure is then applied to the balloon. After cooling and removal of the casing and sleeve, the stent is embedded in the balloon.

The above-described, known methods have the disadvantage that they require relatively long heating and cooling times and are complex on account of the necessary mounting of the sleeve over the assembly. In addition, there is a risk of cross-contamination in the case of implants with a medicament layer.

SUMMARY OF THE INVENTION

A preferred method for embedding a balloon, arranged on a catheter, in an implant having an open-work structure consists of: producing an assembly consisting of the catheter with the balloon and the implant mounted on the outer side of the balloon, inserting the assembly into a cavity of an embedding mold, which is lined on its inner wall with a protective film, wherein the protective film is strip-like, and a width of the protective film is greater than the circumference of the cavity, connecting the catheter to a fluid source, heating the embedding mold with the assembly in a heating element for a predefined time, applying internal pressure to the balloon by the fluid source, cooling the embedding mold with the assembly with a predefined second internal pressure in the balloon, deflating the balloon after cooling the embedding mold with the assembly, and removing the from the mold.

BRIEF DESCRIPTION OF THE DRAWINGS

Further objectives, features, advantages and possible applications of the invention will become clear from the following description of an exemplary embodiment of the device according to the invention and of the method according to the invention with reference to the drawings. Here, all features described and/or depicted in the drawings form the subject matter of the present invention, both individually and in any combination, also independently of their summary in the individual claims and the dependency references of the claims.

The drawings schematically show

DETAILED DESCRIPTION OF THE PREFERRED EMBODIMENTS

Figure 1:
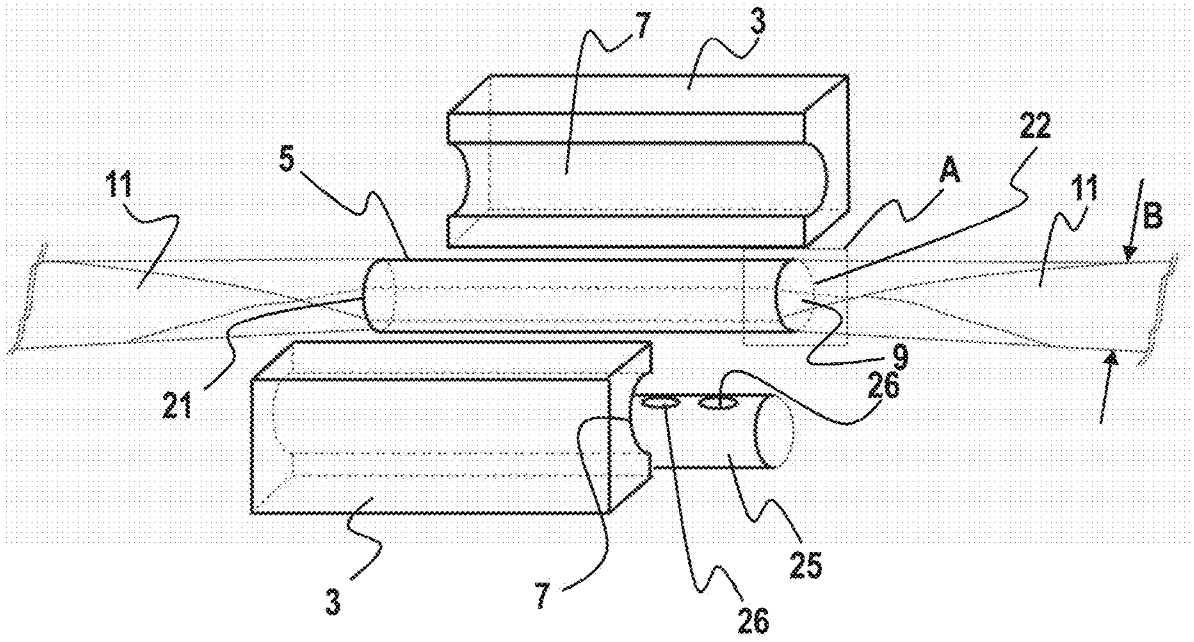
FIG. 1 a device according to the invention in a perspective view from the side, FIG. 2 the embedding mold with protective film of the device according to FIG. 1 in a perspective view from the side, FIG. 3*a* a first step of an exemplary embodiment of a method according to the invention on the basis of a longitudinal section through the embedding mold and protective film, FIG. 3*b* a second step of the method according to FIG. 3*a* with a longitudinal section through an assembly, and FIG. 3*c* a third step of the method according to FIG. 3*a* with a longitudinal section through an assembly.

The protective film between an inner wall of the cavity of the embedding mold and the assembly in preferred devices facilitates the insertion and removal of the assembly into and from the cavity of the embedding mold. The low thickness, that is to say the thin wall, of a preferred protective film means that the heat insulation between heating element and assembly is minimal, so that the assembly is quickly heated and cooled. As a result, the process as a whole is thus accelerated and production costs are consequently saved. The protective film preferably has a thickness of less than 25 μm, particularly preferably of less than 20 μm. The thickness of the protective film is the smallest dimension of the measurements of the protective film.

In one exemplary embodiment of the present invention, the protective film is strip-like. The assembly can thus be particularly easily introduced into and removed from the embedding mold. Alternatively, the protective film can be formed as a layer arranged on the inner wall of the embedding mold. This is a particularly economical solution for the embedding mold.

The insertion and removal of the assembly and also the embedding are designed particularly simply and in an automatable manner if the cavity of the embedding mold runs parallel to the longitudinal direction of the embedding mold and is formed continuously, wherein the strip-like protective film bears loosely against the inner wall of the embedding mold, that is to say is not connected to the inner wall, and can be wound and/or unwound around the assembly and preferably protrudes beyond the continuous cavity of the embedding mold on both sides in the longitudinal direction of the cavity. The strip-like protective film can preferably be unwound from a roll, guided through the continuous is cavity of the embedding mold, and wound onto a roll after use. A new portion of the protective film is used with each assembly in which the implant is to be embedded in the balloon, so that each portion of the protective film is used only once for the embedding. Contaminations and mechanical damage to the externally arranged elements of the assembly are thus avoided.

In order to ensure that the protective film securely surrounds the entire assembly, the width of the strip-like protective film in a preferred exemplary embodiment is greater than the circumference of the cavity of the embedding mold. It is thus ensured that the entire inner wall of the embedding mold is covered. The width of the protective film is measured perpendicularly to the longitudinal direction of the strip. By way of example, the width of the protective film is at least 105% of the circumference, preferably at least 110% of the circumference of the cavity of the embedding mold. Particularly good properties with regard to the insertion and removal of the assembly into/from the cavity of the embedding mold are ensured if the protective film consists of a plastic material, preferably at least one material of the group comprising fluoropolymers (for example polytetrafluoroethylene, perfluoroalkoxy polymers) and polyolefins (for example polyethylene, polypropylene).

It has already been explained above that it is advantageous if the embedding mold has a high heat flux. This requirement can be achieved primarily by a thin-walled geometry (low mass) and by a material having a high thermal conduction coefficient, preferably having a thermal conduction coefficient of more than 10 W/(m*K). On account of the high strength of metallic materials, metallic embedding molds can be designed with particularly thin walls, and therefore a metallic material is preferred for the embedding mold. By way of example, a wall thickness of less than 0.2 mm is possible for aluminium alloys, or less than 0.1 mm for high-grade steel (for example 1.4310). In addition, metallic materials offer high thermal conduction coefficients of more than 10 W/(m*K), whereby quick heating and cooling times and therefore minimal process times are made possible. By way of example, high-grade steel (for example 1.4301, 1.4310), aluminium or aluminium alloy can be used as a material for the embedding mold.

For quick cooling and therefore a reduced process time, a cooling element is is preferably arranged beneath the heating element, which cooling element has, on its upper side, at least one recess for the conduction of a cooling fluid (for example water or a gas, for example in the form of cooled nitrogen). The heating element can preferably be formed in two parts, wherein both parts are joined together to heat the assembly and to close the embedding mold. After the embedding, the two parts of the heating element can be opened again, so that the embedding mold with the assembly is accessible for the cooling fluid.

The above invention is also achieved by methods for embedding a balloon, arranged on a catheter, in an implant having an open-work structure, said method having the following steps:

- producing an assembly consisting of a catheter with balloon and the implant mounted on the outer side of the balloon, preferably by crimping the implant onto the balloon, in particular onto a middle portion of the balloon,
- inserting the assembly into a cavity of an embedding mold, which is lined on its inner wall with a protective film,
- connecting the catheter to a fluid source,
- heating the embedding mold with assembly in a heating element for a predefined time,
- applying a predefined first internal pressure to the balloon by means of the fluid source connected to the catheter,
- cooling the embedding mold with the assembly with a predefined second internal pressure in the balloon, said pressure being applied by means of the fluid source,
- deflating (deaerating) the balloon after cooling the embedding mold with the assembly,
- removing the assembly from the embedding mold.

The preferred method according to the invention allows a quick and economical embedding of the implant in the balloon.

It is also advantageous if, prior to the introduction of the assembly into the cavity of the embedding mold, a strip-like protective film is wound around the assembly. The insertion of the assembly into the cavity of the embedding mold is facilitated as a result.

The removal is facilitated, and mechanical damage and cross-contamination are reduced if, when introducing the assembly into the embedding mold and/or removing the assembly from the embedding mold, the assembly is introduced into the cavity of the embedding mold and/or is removed from the cavity of the embedding mold together/jointly with the strip-like protective film. This means that the relative speed between assembly and protective film is zero in each case, that is to say that the assembly and protective film move at the same speed during introduction and/or removal. The protective film is more preferably unwound from the assembly following the removal.

As has already been described above, the embedding method is facilitated in that the strip-like protective film is unwound from a roll, is guided through the cavity of the embedding mold, and is wound up again onto a further roll, preferably after use for a single assembly.

The device according to the invention shown in FIG. 1 for embedding a balloon 30 of a catheter 29 in an open-work implant, for example a stent 31, has a two-part heating element 3, in which a hollow-cylindrical embedding mold 5 is arranged. For this purpose, corresponding cavities 7 are provided in each part of the heating element 3. The heating element 3 is designed so that it can transfer heat to the embedding mold 5, for example by means of radiation, convection, or contact. For this purpose, the heating element 3 can be designed for example as a resistance heater, induction heating element, capacitive heating element, or as a heating element that works with infrared radiation.

In order to embed a balloon 30, arranged in a catheter 29, in an implant in the form of a stent 31 which has an open-work structure (gaps) at least in portions, an assembly consisting of the stent 31 mounted on the balloon 30 and of the balloon 30 with catheter 29 (see FIGS. 3*b* and 3*c*) is introduced into the continuous cavity 9 of the embedding mold 5. In order to achieve a good transfer of heat from the heating element 3 to the embedding mold 5, the mold consists of a thin-walled geometry (see above) and a material having a high thermal conduction coefficient, for example a metallic material (for example high-grade steel, an aluminium alloy, or aluminium), or very thin-walled glass.

Figure 2:
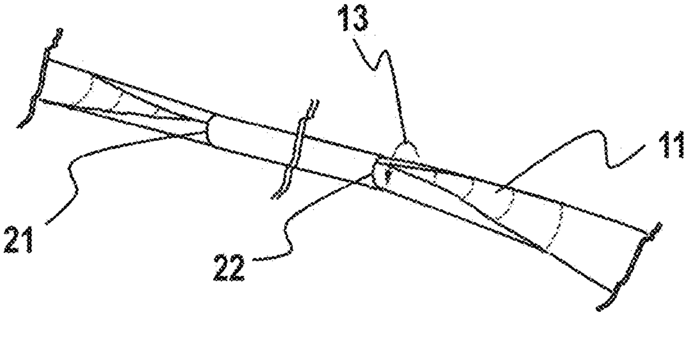
Figure 3A:
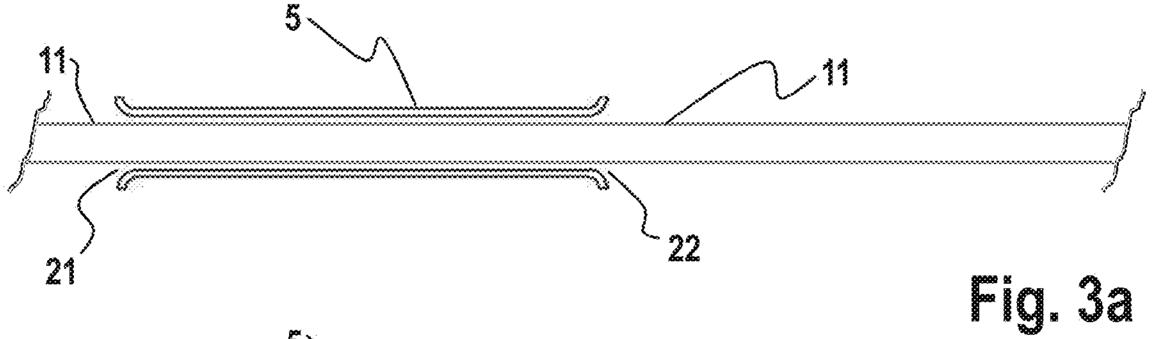

As shown in FIG. 3*a*, a strip-like protective film 11 is guided through the embedding mold 5 and for example can be unwound from a roll (not depicted) and can be wound up again onto a roll (not depicted) once it has been passed through the embedding mold 5. The protective film 11 is laid within the continuous cavity 9 of the embedding mold 5 by a twisting movement (see arrow 13 in FIG. 2 and detail A in FIG. 1) in such a way that the protective film 11 (as considered in cross-section) forms an overlapping "O" so to speak, which bears internally against the inner wall of the continuous cavity 9 of the embedding mold 5 and externally against the assembly. For this purpose, the protective film 11, which preferably consists of a PTFE material, has a width B that is greater than the circumference of the embedding mold 5 along the inner wall thereof.

Figure 3B:
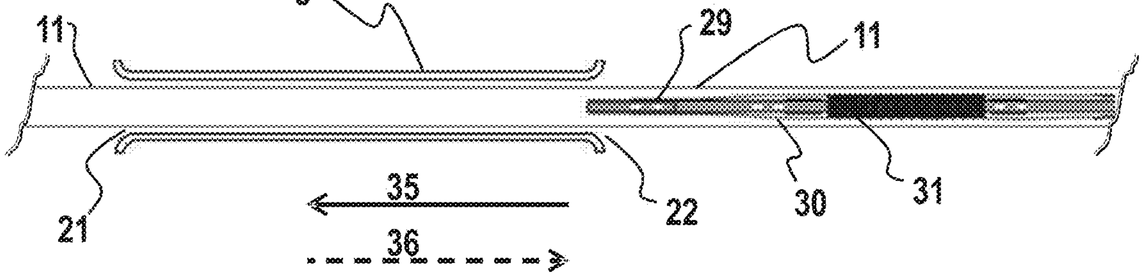

The assembly, as illustrated in FIG. 3*b*, is preferably inserted into the inner volume of the protective film 11, formed by the laying of the protective film 11 against the inner wall of the cavity, before an end 22 of the embedding mold 5 and is then introduced into the embedding mold 5 together with the protective film 11 by drawing the protective film 11 through the cavity 9 of the embedding mold 5. The direction of the joint movement of assembly and protective film 11 is denoted in FIG. 3*b* by the arrow 35. The assembly consisting of the catheter 29 with balloon 30 and the implant mounted on the outer side of the balloon, for example a stent 31, was manufactured beforehand by crimping the stent 31 onto a middle region of the balloon 30.

Figure 3C:
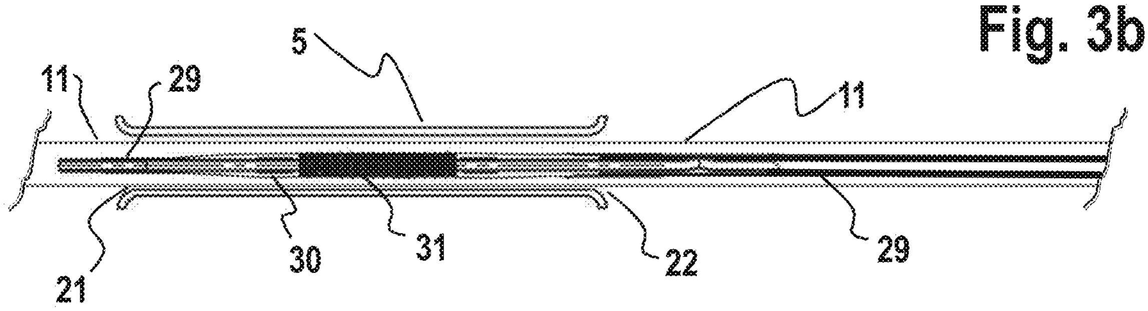

By lining the continuous cavity 9 with the protective film 11, neither the balloon 30 nor the stent 31 comes into contact with the material of the embedding mold 5, and therefore there is no mechanical abrasion created there, that is to say no frictional and/or shear forces between assembly and embedding mold 5. Once the assembly has been fully introduced into the continuous cavity 9 of the embedding mold 5 (position as shown in FIG. 3*c*), each part of the two-part heating element 3 is moved towards the embedding mold 5 and encloses this preferably completely. At the same time, the catheter 29 is connected to a fluid source. The assembly arranged in the embedding mold 5 is now heated by means of the heating element 3 to a predefined temperature, which usually lies above the glass transition point of the balloon material (approximately 55° C. to 150° C.). The internal pressure in the balloon 30 is then increased (approximately 5 to 30 bar) by means of the fluid source connected to the catheter 29, so that the balloon expands slightly. The balloon material is thereby pressed into the gaps of the stent 31 and thus embedded in the stent 31. With continuously applied internal pressure, both parts of the heating element 3 are then removed again from the embedding mold 5, and the embedding mold 5 can cool down. The cooling process can be assisted by a cooling element 25 arranged beneath the embedding mold 5 or the heating element 3, with a cooling fluid, for example air, being conducted to the embedding mold 5 through the pipe of the cooling element and openings 26 arranged on the upper side. A quicker cooling of the embedding mold 5 with the assembly can be achieved as a result.

After sufficient cooling, that is to say usually beneath the glass transition point of the balloon material (for example beneath 55° C.), the pressure in the catheter 29 is reduced again to ambient pressure by the fluid source, and the assembly together with the protective film 11 is removed from the embedding mold 5. The direction of the joint movement of protective film 11 and assembly is depicted in FIG. 3*b* by the arrow 36. A new portion of the protective film 11 is then automatically placed in the embedding mold 5 for the next embedding process. For this purpose, the protective film can be moved further (what is known as an empty run) for example by being drawn through the embedding mold 5 in the direction of the arrow 36 (see FIG. 3*b*). Cross-contamination, for example by medicaments applied to the surface of the stent, is avoided as a result.

Outside the embedding mold 5, the strip-like protective film 11 can be easily torn off, so that the assembly with the balloon 30 embedded in the stent 31 can be easily removed. Mechanical abrasion (that is to say frictional and/or shear loads) at the assembly, in particular at the stent 31, is avoided as a result.

As has already been explained above, the protective film 11 is moved further through the continuous cavity 9 of the embedding mold 5 for the next embedding process, so that a new portion of the protective film 11 is used for the next embedding process. The used protective film is, for example, wound up again on a roll after having been guided through the cavity 9 of the embedding mold 5.

The protective film 11 can consist for example of a plastic material, such as PTFE, PFA, PE, PP, PA, etc. In particular, fluoropolymers have suitable properties with regard to temperature resistance and coefficient of friction.

The above-described device according to the invention and the method according to the invention allow a quick and economical embedding of a stent 31 in a balloon 30.

LIST OF REFERENCE SIGNS

3 heating element
5 embedding mold

7 cavity
9 cavity
11 protective film
13 arrow
21 first end of the embedding mold
22 second end of the embedding mold
25 cooling element
26 opening
30 balloon
31 stent
29 catheter
35 arrow
36 arrow
A detail from FIG. 1
B width of the protective film 11

The invention claimed is:

1. A method for embedding a balloon, arranged on a catheter, in an implant having an open-work structure, said method consisting of the following steps:

producing an assembly consisting of the catheter with the balloon and the implant mounted on the outer side of the balloon,
unwinding a strip of protective film from a roll,
guiding a portion of the strip of protective film into a cavity of an embedding mold to line the cavity of the embedding mold with the portion of the protective film, wherein a width of the protective film is greater than the circumference of the cavity,
twisting the portion of the protective film in the cavity such that the portion of the protective film forms an overlapping "O" shape lining the cavity and defines an inner volume of the "O" shape of the portion of the protective film within the cavity,
inserting the assembly into the inner volume of the "O" shape of the portion of the protective film,
connecting the catheter to a fluid source,
heating the cavity of the embedding mold with the assembly with a heating element of the embedding mold for a predefined time,
applying a predefined first internal pressure to the balloon by the fluid source connected to the catheter,
cooling the cavity of the embedding mold with the assembly with a predefined second internal pressure in the balloon,
deflating the balloon after cooling the cavity of the embedding mold with the assembly,
removing the assembly and the portion of protective film with the assembly from the cavity of the embedding mold,
winding the strip of protective film onto another roll.

2. The method according to claim 1, wherein the protective film has a thickness of less than 25 μm.

3. The method according to claim 1, wherein the protective film comprises at least one material selected from the group consisting of fluoropolymers and polyolefins.

4. The method according to claim 3, wherein the fluoropolymers are selected from the group consisting of polytetrafluoroethylene and perfluoroalkoxy polymers.

5. The method according to claim 4, wherein the polyolefins are selected from the group consisting of polyethylene and polypropylene.

6. The method according to claim 1, wherein the embedding mold has a thermal conduction coefficient of more than 10 W/(m*K).

7. The method according to claim 6, wherein the cavity in the embedding mold has a wall thickness of less than 0.2 mm.

8. The method according to claim 1, wherein the cavity is continuous and parallel to the longitudinal direction of the embedding mold, wherein the protective film protrudes the cavity on both of opposite sides of the cavity in the longitudinal direction.

9. The method according to claim 1, wherein the protective film is plastic material selected from the group consisting of PTFE, PFA, PE and LDPE.

10. The method according to claim 1, wherein the twisting comprises a rotational movement around an axis parallel to a direction of the guiding of the portion of the strip of protective film into the cavity of the embedding mold.

11. The method according to claim 1, wherein the removing and winding cause additional unwinding to move another portion of the protective film into the cavity and then the remaining steps of claim 1 are repeated.

12. A method for embedding a balloon, arranged on a catheter, in an implant having an open-work structure, said method consisting of the following steps:

producing an assembly consisting of the catheter with the balloon and the implant mounted on the outer side of the balloon,
unwinding a strip of protective film from a roll,
guiding a portion of the strip of protective film into a cavity of an embedding mold with the assembly to line the cavity of the embedding mold with the portion of the protective film and place the assembly in the cavity, wherein a width of the protective film is greater than the circumference of the cavity,
twisting the portion of the protective film in the cavity such that the portion of the protective film forms an overlapping "O" shape lining the cavity and defines an inner volume of the "O" shape of the portion of the protective film within the cavity to enclose the assembly within the inner volume of the "O" shape of the portion of the protective film,
connecting the catheter to a fluid source,
heating the cavity of the embedding mold with the assembly with a heating element of the embedding mold for a predefined time,
applying a predefined first internal pressure to the balloon by the fluid source connected to the catheter,
cooling the cavity of the embedding mold with the assembly with a predefined second internal pressure in the balloon,
deflating the balloon after cooling the cavity of the embedding mold with the assembly,
removing the assembly and the portion of protective film with the assembly from the cavity of the embedding mold,
winding the strip of protective film onto another roll.

13. The method according to claim 12, wherein the twisting comprises a rotational movement around an axis parallel to a direction of the guiding of the portion of the strip of protective film into the cavity of the embedding mold.

14. The method according to claim 12, wherein the removing and winding cause additional unwinding to move another portion of the protective film into the cavity and then the remaining steps of claim 1 are repeated.

* * * * *